United States Patent
Willis et al.

(10) Patent No.: US 11,284,927 B2
(45) Date of Patent: Mar. 29, 2022

(54) ORTHOPEDIC SCREW AND POROUS STRUCTURES THEREOF

(71) Applicant: Stryker European Holdings I, LLC, Kalamazoo, MI (US)

(72) Inventors: Steven Willis, Mahwah, NJ (US); Steven F. Krause, Oakland, NJ (US); Amir Ali Sharifi-Mehr, Bloomingdale, NJ (US); Brett Traficant, Wyckoff, NJ (US); Erika Corbin, Mahwah, NJ (US); Lauren Barkauskas, Pittsburgh, PA (US)

(73) Assignee: Stryker European Holdings I, LLC, Kalamazoo, MI (US)

( * ) Notice: Subject to any disclaimer, the term of this patent is extended or adjusted under 35 U.S.C. 154(b) by 0 days.

(21) Appl. No.: 16/263,068

(22) Filed: Jan. 31, 2019

(65) Prior Publication Data

US 2019/0239935 A1    Aug. 8, 2019

Related U.S. Application Data

(60) Provisional application No. 62/625,541, filed on Feb. 2, 2018.

(51) Int. Cl.
*A61B 17/86* (2006.01)
*A61B 17/70* (2006.01)
*A61F 2/28* (2006.01)

(52) U.S. Cl.
CPC ...... *A61B 17/8605* (2013.01); *A61B 17/7032* (2013.01); *A61B 17/864* (2013.01); *A61B 17/8625* (2013.01); *A61B 17/7002* (2013.01); *A61F 2002/2835* (2013.01); *A61F 2310/00023* (2013.01)

(58) Field of Classification Search
CPC .............. A61B 17/8605; A61B 17/861; A61B 17/8625; A61B 17/8635; A61B 17/864; A61B 2017/8655
See application file for complete search history.

(56) References Cited

U.S. PATENT DOCUMENTS

| 5,226,766 A * | 7/1993 | Lasner ................. A61B 17/863 411/308 |
| 5,360,448 A | 11/1994 | Thramann |
| 6,488,681 B2 | 12/2002 | Martin et al. |
| 7,686,834 B2 | 3/2010 | Saint Martin |

(Continued)

FOREIGN PATENT DOCUMENTS

WO    2016082880 A1    6/2016

OTHER PUBLICATIONS

ES2® Spinal System, Stryker Spine, Copyright 2016, 64 pages.

(Continued)

*Primary Examiner* — Anu Ramana
(74) *Attorney, Agent, or Firm* — Lerner, David, Littenberg, Krumholz & Mentlik, LLP (57) ABSTRACT

A bone fastener includes a head, and a screw portion extends from the head. The screw portion includes a shaft and a thread extending along and about the shaft. The thread has a height extending from a root to a tip thereof. The thread also has first and second portions disposed between the root and the tip. The second portion has a porous structure configured to promote bone ingrowth and has a porosity greater than that of the first portion.

9 Claims, 3 Drawing Sheets

(56) References Cited

U.S. PATENT DOCUMENTS

| | | | |
|---|---|---|---|
| 7,935,138 B1* | 5/2011 | Richelsoph | A61B 17/8625 |
| | | | 606/313 |
| 8,007,520 B2 | 8/2011 | Metz-Stavenhagen | |
| RE42,932 E | 11/2011 | Martin et al. | |
| 8,292,967 B2 | 10/2012 | Brown et al. | |
| RE45,338 E | 1/2015 | Chin et al. | |
| 8,979,911 B2 | 3/2015 | Martineau et al. | |
| 9,101,427 B2* | 8/2015 | Globerman | A61B 17/80 |
| 9,370,388 B2* | 6/2016 | Globerman | A61B 17/8033 |
| 9,408,716 B1 | 8/2016 | Reitblat et al. | |
| 9,636,229 B2* | 5/2017 | Lang | A61F 2/389 |
| 2006/0111715 A1 | 5/2006 | Jackson | |
| 2006/0276788 A1* | 12/2006 | Berry | A61B 17/7059 |
| | | | 606/286 |
| 2010/0042215 A1 | 2/2010 | Stalcup et al. | |
| 2012/0277804 A1* | 11/2012 | Bhatnagar | A61B 17/864 |
| | | | 606/298 |
| 2014/0277188 A1* | 9/2014 | Poulos | A61B 17/8635 |
| | | | 606/304 |
| 2015/0209094 A1 | 7/2015 | Anderson | |
| 2016/0000489 A1 | 1/2016 | Kaloostian | |
| 2016/0157908 A1 | 6/2016 | Cawley et al. | |
| 2016/0166301 A1 | 6/2016 | Papangelou et al. | |
| 2016/0199193 A1 | 7/2016 | Willis et al. | |

OTHER PUBLICATIONS

Xia® 3 Spinal System, Stryker Spine, Copyright 2016, 56 pages.
European Search Report including Written Opinion for Application No. EP19154661.3, dated Mar. 2, 2020, pp. 1-9.
Partial European Search Report including Provisional Opinion for Application No. EP19154661.3, dated Nov. 22, 2019, pp. 1-12.

* cited by examiner

ORTHOPEDIC SCREW AND POROUS STRUCTURES THEREOF

CROSS-REFERENCE TO RELATED APPLICATIONS

This application claims the benefit of the filing date of U.S. Provisional Patent Application No. 62/625,541, filed Feb. 2, 2018, the disclosure of which is hereby incorporated herein by reference.

FIELD OF THE INVENTION

The present invention relates to bone screws and more particularly to bone screws having a partially porous structure for promoting bone growth therein.

BACKGROUND OF THE INVENTION

Bone screws are utilized in a wide variety of orthopedic applications including procedures in which the bone screws are used to reduce bone fragments or to connect one or more structures to a bone. In this regard, it is desirable for such bone screws to maintain their respective positions within a bone for extended periods of time including for the life of the patient. While certain existing bone screws may be utilized with plates, implants or the like that employ back-out prevention features, there exists a continued need for improved fixation within the bone.

BRIEF SUMMARY OF THE INVENTION

The present disclosure describes exemplary embodiments of bone screws that include both solid and porous portions. The porous portions of these screws promote bone ingrowth to help facilitate long term fixation of such screws, while the solid portions provide structural support. Moreover, the solid and porous portions each comprise an exterior of each of the described screws such that the solid and porous portions come in contact with bone when applied thereto. In this regard, the ratio of bone contacting surface area defined by the porous portions relative to that of the solid portions may be predetermined such that the amount of bone growth into the porous portions is controlled so that the removal torque of the screw can be overcome by ordinary surgical instruments even after ingrowth has occurred over an extended period of time in order to remove the screw from the bone without having to cut the bone surrounding the screw. The bone screws described herein may be made via an additive manufacturing process, which can allow the porous portions to be disposed in locations on the screw difficult or impossible to achieve by other manufacturing processes and so that the porous and solid portions are integrated with each other to form a unitary/monolithic screw.

In one aspect of the present disclosure, a bone fastener includes a head, and a screw portion extending from the head. The screw portion includes a shaft and a thread extending along and about the shaft. The thread having a height extending from a root to a tip thereof. The thread also having first and second portions disposed between the root and the tip. The second portion includes a porous structure configured to promote bone ingrowth and having a porosity greater than that of the first portion.

Additionally, the height of the thread may increase toward a distal end of the bone fastener. Also, the shaft may taper inwardly toward the distal end of the bone fastener. The first portion of the thread may be positioned further from the shaft than the second portion. Moreover, the first portion and the second portion may collectively define an outer bone contacting surface of the thread, and the first portion may have a solid structure.

Continuing with this aspect, a height of the second portion may be constant along a length of the shaft. Also, a height of the first portion may increase toward a distal end of the bone fastener. The height of the thread may include the heights of the first portion and second portion. A height of the second portion may be about 0.5 mm or greater. The head, shaft and first portion of the thread may each comprise a solid structure that has a porosity smaller than that of the second portion.

In another aspect of the present disclosure, a bone fastener includes a head, and a screw portion extending from the head. The screw portion includes a shaft and a thread extending helically along and about the shaft and defines a helical depression therebetween. The screw portion also includes a plurality of porous fenestrations disposed within the helical depression and extends into the shaft. The porous fenestrations are filled with a porous structure configured to promote bone ingrowth. The porous structure includes a portion of an external surface of the bone fastener and is surrounded by a solid structure having a porosity smaller than that of the porous structure. Also a porous liner at least partially surrounds the channel and is disposed within the shaft of the screw portion. The porous liner includes a porous structure interconnected within the porous structure of at least two of the porous fenestrations.

Additionally, the porous fenestrations may each define a circular opening having a diameter of 0.5 to 1.2 mm 12. The porous fenestrations may extend into the shaft 0.5 mm or greater. The bone fastener may further include a channel extending along the length of the bone fastener and through both the screw portion and head of the bone fastener. At least some of the porous fenestrations may extend through the shaft and into communication with the channel such that the porous structure extends from the channel to an exterior of the bone fastener.

Continuing with this aspect, each porous fenestration may be offset from an adjacent porous fenestration by 10 to 90 degrees about a longitudinal axis of the bone fastener. Each porous fenestration may be offset from an adjacent porous fenestration by 20 degrees about a longitudinal axis of the bone fastener. A bone fastener may include a head, first and second screw portions each including a shaft, and a thread extending along and about the shaft. A shank may be disposed between the first and second screw portions. The shank may be threadless and having a plurality of porous portions interspersed within a solid substrate such that an exterior surface is both solid and porous. The plurality of porous portions may be a plurality of fenestrations that extend into the solid substrate of the shank and may be filled with a porous structure that is configured to promote bone ingrowth. The fenestrations may be helically arranged about the shank. The porous fenestrations may each define a circular opening having a diameter of 0.5 to 1.2 mm 21 The porous portions may extend into the solid substrate about 0.5 mm or greater.

In a further aspect of the present disclosure, a bone fastener includes a screw portion having a shaft and a thread, and a head positioned at a proximal end of the screw portion. The head includes a proximal portion and a distal portion. The distal portion of the head defines a bone contacting surface that faces in a direction toward a distal end of the screw portion. The distal portion has a porous structure configured to promote bone ingrowth and has a porosity greater than that of the proximal portion and the screw portion. The distal portion of the head defines a porous ring that extends about a longitudinal axis of the bone fastener.

Additionally, the porous structure of the distal portion may extend partially into a solid structure of the head. The head may be tulip shaped and may have a slot extending through the head in a direction transverse to a longitudinal axis of the screw, the slot may be configured to receive a spinal rod therein. The head may include a threaded inner surface.

BRIEF DESCRIPTION OF THE DRAWINGS

The features, aspects, and advantages of the present invention will become better understood with regard to the following description, appended claims, and accompanying drawings in which:

DETAILED DESCRIPTION

As used herein, when referring to the disclosed devices, the term "proximal" means closer to the operator or in a direction toward the operator and the term "distal" means more distant from the operator or in a direction away from the operator. Also, as used herein, the terms "about," "generally," and "substantially" are intended to mean that slight deviations from absolute are included within the scope of the term so modified.

FIGS. 1A-1D depict a cannulated bone screw 100 according to an embodiment of the present disclosure. Bone screw 100 generally includes a head 110, screw portion 120 extending from head 110, and a channel 130 extending through screw portion 120 and head 100. Such channel 130 may be configured to receive a k-wire and/or a flowable material such as bone cement, medicament, bone marrow aspirate, and the like. However, in some embodiments, screw 100 may not include channel 130.

Head 110 includes an underside 112 and a topside 114. Underside 112 defines a first radial surface 115. Topside 114 includes an upward extending post 113 and a plurality of downwardly extending grooves 111 (see FIG. 1B) positioned about post 113. Such grooves 111 are adapted to engage a complementary driver tool. However, other configurations for engaging a driver tool that are known in the art are contemplated. Post 113 defines a second radial surface 117 that has a radius smaller than that of first radial surface 115. In this regard, head 110 is a dual radius head which is configured to be driven by a driver while also being configured to polyaxially anchor other components to a bone, such as a stabilizing rod and coupling element to a vertebra. Examples of screws similar to screw 100, as well as components, such as stabilizing rods, coupling elements, and drivers, that can be used in conjunction with screw 100 are disclosed in U.S. Pat. Nos. RE42,932; 6,488,681; 7,686,834; 8,231,635; RE45,338; and 9,408,716, the entireties of which are incorporated by reference herein and all of which are assigned to the same entity as the present invention. However, it is to be understood that the present invention can be utilized in a connection with any type of screw designed to be implant into bone.

Figure 1A:
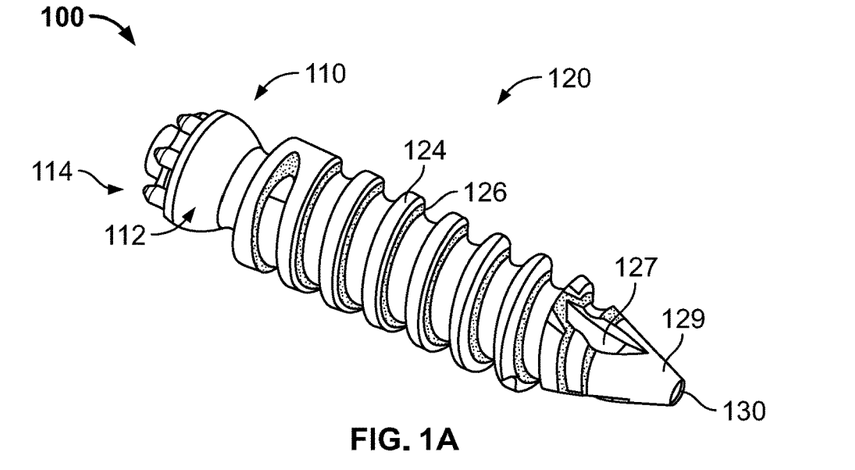
FIG. 1A is a perspective view of a bone screw according to an embodiment of the present disclosure.
Figure 1B:
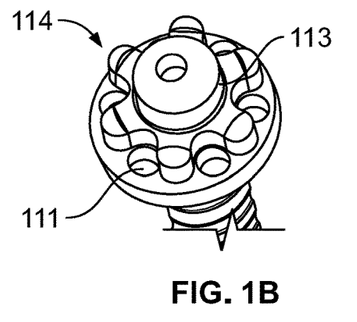
FIG. 1B is a perspective view of a head of the bone screw of FIG. 1A.

Screw portion 120 extends distally from head 110 and includes a shaft 128, helical thread 122, distal tip 129, and one or more cutting flutes 127. Shaft 128 extends from head 110 and tapers inwardly toward a distal end of screw 100. Shaft 128 also defines a minor diameter of screw. In this regard, the minor diameter of screw 100 gradually decreases in a distal direction. Distal tip 129 extends distally from shaft 128 and is also tapered in the distal direction. As depicted distal tip 129 is threadless. However, in some embodiments distal tip 129 may be fully or partially threaded. Cutting flutes 127 may extend along both shaft 128 and distal tip 129 to facilitate self-tapping. However, in some embodiments, particularly those that are not self-tapping, screw 100 may not include a cutting flute.

Figure 1C:
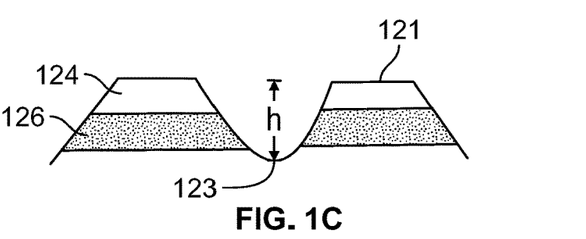
FIG. 1C is a schematic view of a thread of the screw of FIG. 1A.
Figure 1D:
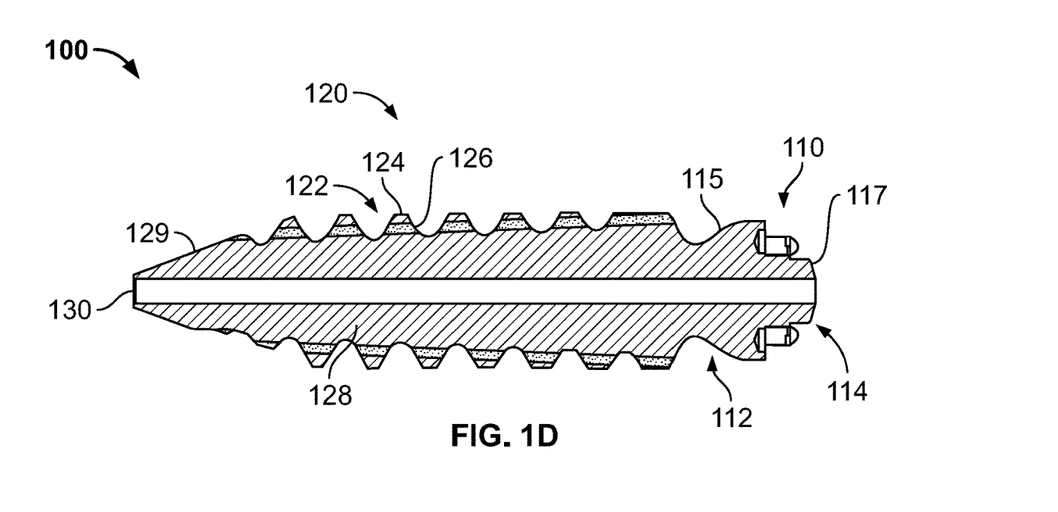
FIG. 1D is a cross-sectional view of the bone screw of FIG. 1A taken along a midline thereof.

Thread 122 of screw 100 helically extends along and about shaft 128. Thread 122 has a height (h) defined between a root 123 and a crest 121 of thread 122, as depicted in FIG. 1C. Thread 122 has a single start and defines a major diameter of screw 100. However, in some embodiments, screw 100 may include multiple threads defining multiple starts. In the particular embodiment depicted, the major diameter is constant along the length of the majority of shaft 128. Thus, because the taper of shaft 128 and the constant outer diameter of thread 122, the root 123 to crest 121 height (h) of thread 122 increases in a distal direction, as is best shown in FIG. 1D. However, it should be understood that screw 100 may have other configurations, such as a constant minor diameter and a variable major diameter, or a constant major and minor diameter.

Thread 122 includes a first portion 124 and a second portion 126 between root 123 and crest 121. First portion 124 and second portion 126 are positioned adjacent each other with first portion 124 positioned further from shaft 128 than second portion 126. In this regard, first portion 124 is positioned at a radial extent of thread 122 and defines crest 121. Second portion 126 is positioned adjacent to shaft 128 at a base of thread 122. However, at a distal end of thread 122 near the start of thread 122, first portion 124 may not be positioned over second portion 126, as shown in FIG. 1A.

First portion 124 has solid structure, while second portion 126 has a porous structure. The porous structure of second portion 126 has a porosity that promotes bone ingrowth over time when tissue is in contact therewith, as well as to aid in initial fixation prior to ingrowth. For example, the porous structure of second portion 126 may have an average pore diameter between 20-1000 microns with a 30-80% porosity. However, preferably the porosity may be between 55-65% and may either be constant throughout the porous structure or gradient such that the porous structure has a varying porosity. In contrast, the solid structure of first portion 124, to the extent it may have a porosity, does not have a porosity that promotes bone ingrowth and has therefore has a porosity less than that of the porous structure of second portion 126 and generally no porosity whatsoever. However, the solid structure of first portion 122 provides strength and stability to thread under different loading conditions. The remainder of screw 100 other than thread 122, which includes head 110, shaft 128, and distal tip 129, may have a solid structure similar to that of first portion 124 of thread 122. The porous portions of screw 100, as well as the solid portions thereof, may be formed through use of an additive manufacturing process as described below, and may be made from the same material or different material that is capable of bonding with each other through the additive manufacturing process.

Porous second portion 126 has a constant height along the length of shaft 128. As mentioned above, the root-to-tip height (h) of thread 122 increases in the distal direction. Thus, since porous second portion 126 of thread 122 has a constant height along the length of shaft 128, solid first portion 124 of thread 122 has a variable height along the length of shaft 128, as best seen in FIG. 1D. In this regard, the height of first portion 124 decreases in the proximal direction. In other embodiments of screw 100, porous second portion 126 may have a variable height along the length of shaft 128 while solid first portion 124 has a constant height. In even further embodiments of screw 100, first and second portions 124, 126 of thread 122 may each have variable heights along the length of shaft 128. However, it is preferable that that the height of porous portion 126 be about 0.5 mm or greater.

Porous second portion 126 and solid first portion 124 comprise a bone contacting surface that is therefore both porous and solid. In this regard, solid first portion 124 helps provide strength while screw 100 is driven into bone and porous second portion 126 facilitates bone ingrowth at opposite sides of thread 122 to promote long term fixation of screw 100 and to prevent inadvertent backout thereof during the period of time that screw 100 is implanted. However, it may be necessary at some point to remove screw 100 from the bone even after extended periods of time over which bone ingrowth has occurred. In this regard, the surface area of porous structure of second portion 126 that is exposed to bone is proportional to or smaller than that of the surface area exposed to bone of the solid structure 124 so that the resistance afforded by bone ingrowth can be overcome through torsion applied to screw 100 using standard driver instruments. In one embodiment of screw 100, height "h" of thread 122 may be 50% comprised of the porous second portion and 50% of the solid first portion. In other embodiments, the height "h" of thread 122 can comprise 10% to 90% of the surface area of thread.

In a method of use, a driver is engaged to topside 114 and screw 100 is driven into bone, such as a vertebrae. As screw 100 is driven into the bone, solid first portions 124 of thread 122 and thread flute 127 cut through the cortical and cancellous layers of the bone. Once fully seated, the natural roughness of porous second portion 126 of threads 122 may help prevent backout of screw 100 via frictional resistance. Thereafter, implantable equipment may be connected to screw 100, such as components of a spinal rod system or a bone plate for fracture reduction and stabilization, for example. Over time, bone may grow into porous structure 126 of screw 100 helping to further secure screw 100 to the bone. If after a such ingrowth occurs it is necessary to remove screw 100 from the bone via a revision procedure or the like, screw 100 may be reengaged with a driver instrument and rotated such that the bonds formed between screw 100 and bone via bone ingrowth are broken thereby allowing screw 100 to be removed without the need to cut excess bone surrounding screw 100 for its removal.

Figure 2A:
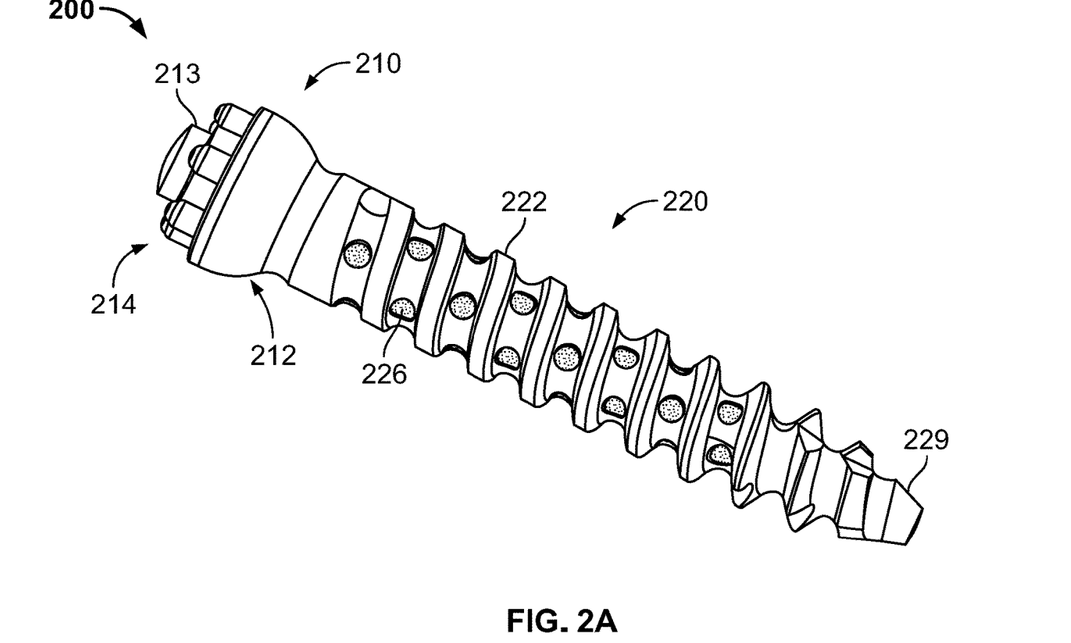
FIG. 2A is a perspective view of a bone screw according to another embodiment of the present disclosure.
Figure 2B:
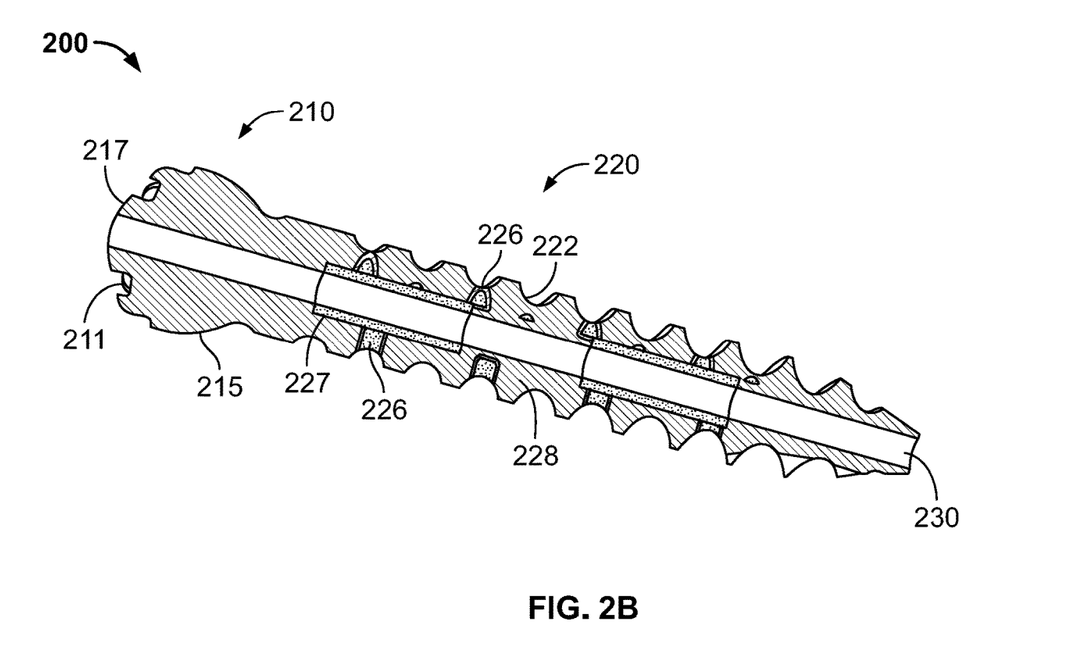
FIG. 2B is a cross-sectional view of the bone screw of FIG. 2A taken along a midline thereof.

FIGS. 2A and 2B depict a screw 200 according to another embodiment of the present disclosure. Screw 200 is similar to screw 100 in that screw 200 includes a head 210, screw portion 220 extending from head 210, and a channel 230 extending through screw portion 220 and head 100. In addition, head 210 is similar to head 110 in that it includes a topside 214 that defines a post 213 and plurality of grooves 211 for engaging a corresponding driver and an underside 212 that defines a radial surface 215 with a radius larger than a radial surface 217 of post 213. Also, screw portion 220 includes a shaft 228, thread 222, and distal tip 229 similar to that of screw 100. However, screw 200 differs with respect to its solid and porous configuration.

As shown, screw 200 includes a plurality of porous fenestrations 226 that extend into shaft 228 from an outer surface thereof and in a helical arrangement between thread 222. In other words, the fenestrations are positioned in a helical depression that is defined by thread 222. Each fenestration 226 may be positioned at a predetermined angle relative to adjacent fenestrations 226. For example, each fenestration may be distributed every 10 to 90 degrees in a helical pattern about screw 200 and relative to each adjacent fenestration 226, but preferably every 20 degrees. Fenestrations 226 are depicted as defining round openings in the solid structure of shaft 228, which may have a diameter 0.5 to 1.2 mm, but preferably 1 mm. However, fenestrations 226 can define various different shaped openings, such as rectangular, ovular, triangular, and the like, for example. Porous fenestrations 226 are filled with a porous structure such that the porous structure forms a portion of an external surface of screw 200 at the respective openings of porous fenestrations 226. As described below, porous fenestrations 226 provide strength to screw 200 relative to a complete absence of structure in fenestrations 226 and allows for bone ingrowth into its porous structure and for injection of materials therethrough, such as bone cement, bone marrow aspirate, and biologics.

In addition to porous fenestrations 226, screw 200 includes one or more porous liners 227 lining channel 230. Such porous liners 227 may be fully cylindrical so as to form a sleeve that has an opening coaxial with channel 230. However, in some embodiments, porous liners 227 may be partially cylindrical and thus may not encircle channel 230. In this regard, liners 227 along with the solid structure of shaft 228 define channel 230. Liners 227 extend along at least a portion of shaft 228 of screw portion 220 and may extend between a plurality of fenestrations 226. Porous liners 226, as shown, do not extend entirely through the radial extent of shaft 228. However, porous liners 226 are preferably in communication with some or all of porous fenestrations 226. In this regard, a flowable material such as bone cement and medicament can be injected through channel 230, porous liners 227, and selected fenestrations 226 so that the bone cement or medicament can be delivered to the bone from multiple locations along the length of screw 200. Alternatively, bone marrow aspirate can be aspirated from the bone from multiple locations along the length of screw 200. Even further, bone graft material can be packed into channel 230 to bolster bone ingrowth.

While porous liners 227 are depicted in FIG. 2B as affording communication of porous fenestrations 227 with channel 230 of screw 200, it is also contemplated that screw 200 may not have porous liners 227 and instead each porous fenestration 226 or a select number thereof may extend entirely through shaft 228 so as to communicate directly with channel 230. In this regard, porous fenestrations 226 may form a uniform column of porous material that extends entirely through shaft 228.

The porous structure of liners 227 and fenestrations 226 is similar to that previously described for promoting bone ingrowth. Additionally, in some embodiments, the porous structure in each fenestration 226 may have the same porosity, while in other embodiments the porosity may differ fenestration-by-fenestration. Moreover, the porosity in each fenestration 226 may be uniform or it may differ such that the porosity of each fenestration 226 increases in an outwardly radial direction. In addition, the remaining features of screw 200 other than porous fenestrations 226 and liners 227 are comprised of a solid structure so as to reinforce screw 200 and provide strength to screw 200 as well as to help control the surface area ratio between the porous and solid structure to allow for bone ingrowth that can be overcome by a predetermined amount of torque applied to screw 200.

In a method of use, a driver is engaged to topside 214 and screw is driven into bone, such as a vertebrae. As screw 200 is driven into the bone, the solid thread 222 cuts into the cortical and cancellous layers of the bone. Once fully seated, bone cement or medicament may be injected or, alternatively, bone marrow aspirated, through channel 230 and porous fenestrations 226 to treat the bone or provide additional fixation support thereto such as described in U.S. application Ser. No. 15/286,039, the disclosure of which are hereby incorporated by reference in their entireties herein. Also, implantable equipment may be connected to screw 200, such as components of a spinal rod system, such as one of the systems mentioned above. Over time, bone may grow into the porous structure 226, 227 of screw 200 helping to further secure screw 200 to the bone. If after a such ingrowth occurs, it is necessary to remove screw 200 from the bone via a revision procedure or the like, screw 200 may be reengaged with a driver instrument and rotated such that the bonds formed between screw 200 and bone via bone ingrowth are broken thereby allowing screw 200 to be removed without the need to cut excess bone surrounding the screw for its removal.

Figures 3, 4, 5:
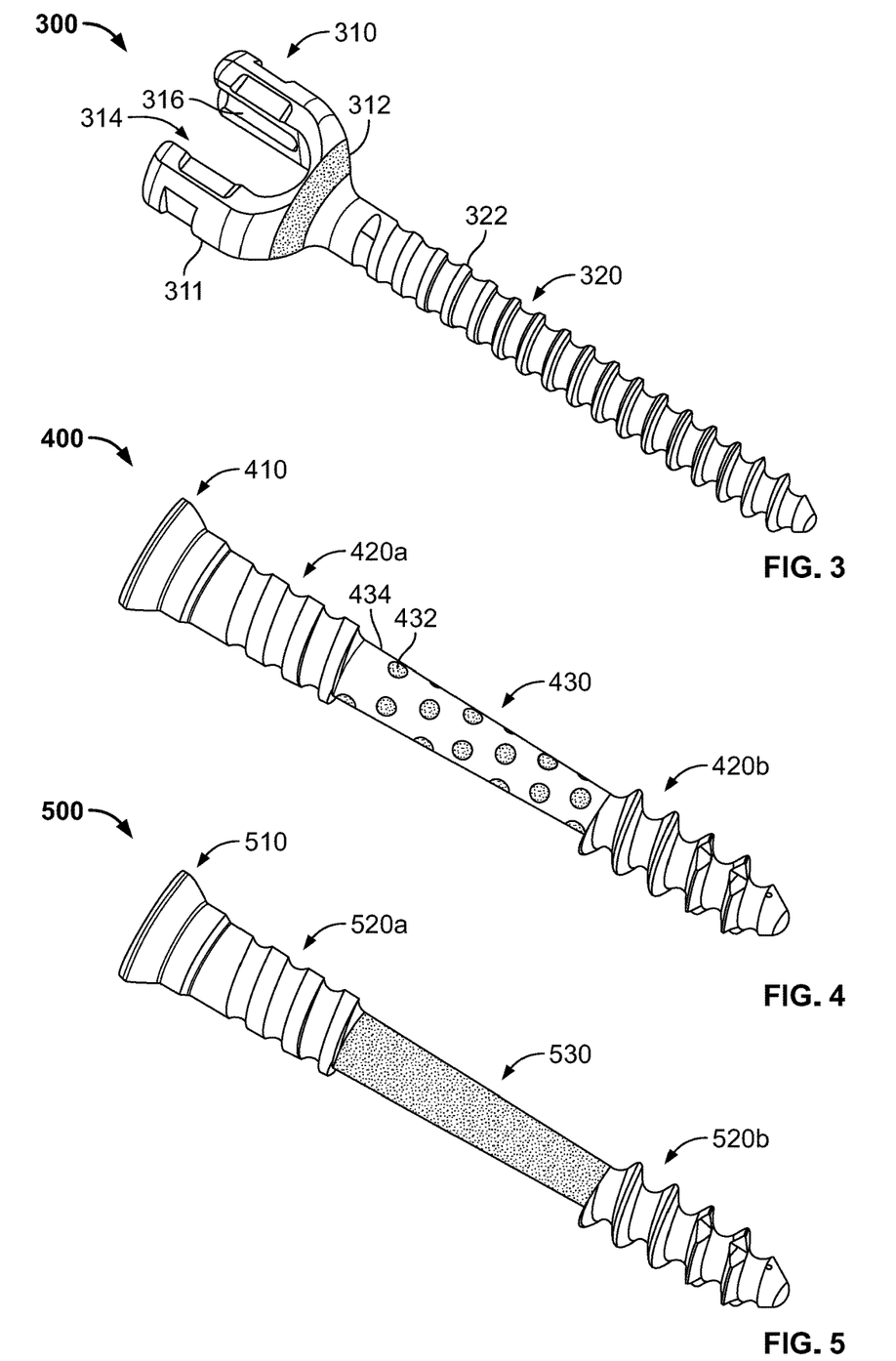
FIG. 3 is a perspective view of a bone screw according to a further embodiment of the present disclosure.
FIG. 4 is a perspective view of a bone screw according to an even further embodiment of the present disclosure.
FIG. 5 is a perspective view of a bone screw according to yet another embodiment of the present disclosure.

FIG. 3 depicts a screw 300 according to a further embodiment of the present disclosure. Screw 300 includes a head 310 and screw portion 320 extending from head 310. Head 310 is a tulip-shaped head that includes a U-shaped slot 314 extending through head 310 and transverse to an axis of screw 300. Such slot 314 is configured to receive a spinal rod therein and may be internally threaded for threaded engagement to a set screw (not shown) or the like, as disclosed in U.S. Pat. No. 8,007,520, the disclosure of which is incorporated by reference herein in its entirety. Head 310 also includes a proximal solid portion 311 and a distal porous portion 312. Distal porous portion 312 comprises a distal end of head 310 adjacent to screw portion 320 of screw 300. In this regard, distal porous portion 312 defines a distally facing surface so that when screw 300 is driven into bone, porous portion 312 sits directly against the bone, such as a transverse process/facet junction. In the embodiment depicted, distal porous portion 312 forms a ring that extends about the axis of screw 300 and has a proximal-distal length of about 0.5 to 2 mm, but preferably 1.75 mm. In addition, distal porous portion 312 does not extend full thickness through head 310 and instead preferably extends into head 310 from the exterior thereof. In this regard, the entire internal surface 316 of head 310 is solid. The distance into which the porous portion 312 extends into head 310 may be about 0.3 to 0.8 mm, but preferably 0.5 mm. In addition, this distance or thickness of porous portion may vary along the proximal-distal length of porous portion 312 to account for regions of high stress. However, in some embodiments porous portion 312 may span full thickness between inner surface 316 and an exterior of tulip-shaped head 310, such that porous portion 312 comprises a portion of internal surface 316. Also, screw portion 320 may be similar to screw portion 120 with the exception that screw portion 320 may be entirely solid.

In a method of use, a driver is engaged to screw 300, and screw 300 is driven into bone, such as a vertebrae. Once fully seated, distal porous portion 312 is positioned directly against the bone. In this regard, the bone, such as a transverse process/facet junction, may be abraded before screw insertion so that porous portion 312 directly abuts the abraded bone to help facilitate bone ingrowth. Implantable hardware may then be connected to the screw 300. For example, a spinal rod may be inserted into slot 314 such that it extends therethrough in a direction transverse to an axis of screw 300. A set screw may then be threaded to head 310 over the spinal rod for securing rod to screw 300. Over time, bone may grow into porous portion 312 of screw 300 helping to further secure screw 300 to the bone. If after such ingrowth occurs, it is necessary to remove screw 300 from the bone via a revision procedure or the like, all hardware may disengaged from screw 300. Screw 300 may then be reengaged with a driver instrument and rotated such that the bonds formed between distal porous portion 312 and bone via bone ingrowth are broken thereby allowing screw 300 to be removed without the need to cut excess bone surrounding screw 300 for its removal.

FIG. 4 depicts a bone screw 400 according to an even further embodiment of the present disclosure. Screw 400 is a lag screw and has a head 410, first screw portion 420a, second screw portion 420b, and shank 430. Screw 400 may be used with other orthopedic devices, such as bone plates, or by itself. First screw portion 420a is positioned adjacent head 410 while second screw portion 420b is positioned at a distal end of screw 400. Screw 400 may be cannulated, like screw 200, or not cannulated. First and second screw portions 420a-b are threaded and have a solid structure.

Shank 430, which is disposed between first and second screw portions 420a-b, is unthreaded and includes a solid exterior surface 434 that is interrupted by a plurality of porous fenestrations 432 arrayed about shank 430. Fenestrations 432 are similar to fenestrations 226 of screw 200 in that they are organized in a helical pattern with a fenestration 432 positioned every 10 to 90 degrees, but preferably every 20 degrees about shank 430. However, in some embodiments, fenestrations 432 may be arranged in a non-helical pattern, such as in linear rows. Moreover, fenestrations 432 may extend through shank 430 such that they communicate with a channel (not shown) for aspiration of bone marrow aspirate or for delivery of a flowable material to the bone. This may be facilitated by one or more porous liners lining the channel, such as porous liners 227 of screw 200. However, in some embodiments, fenestrations 432 may not extend entirely through shank 430 to the channel or may have fenestrations 432 that communicate with the channel and some that do not. However, where fenestrations 432 do not extend through shank 430 to the channel, fenestrations preferably extend 0.5 mm or greater through the exterior of shank 430.

Fenestrations 432 are shown as defining a round opening, which may have a diameter of 0.5 to 1.2 mm, but preferably 1 mm. Moreover, each fenestration 432 may have the same diameter, or, in some embodiments, fenestrations 432 may have a variable diameter such that some of the fenestrations 432 have a smaller diameter than other fenestrations 432. For example, some of fenestrations 432 may have a diameter of 0.5 mm while others may have a diameter of 1 mm. While fenestrations 432 are shown as defining a round, porous opening in the solid structure of shank 430, fenestrations 432 can define other shaped openings such as a square, ovular, or triangular shaped opening, for example.

FIG. 5 depicts a bone screw 500 according to yet another embodiment of the present disclosure. Screw 500 is similar to that of screw 400 with the exception that shank 530 is entirely porous rather than having porous portions arrayed within a solid exterior. In this regard, screw 500 has a solid head 510, a solid first screw portion 520a, a solid second screw portion 520b, and a porous shank 530 disposed between solid screw portions 530a-b. Porous shank portion 530 may have uniform porosity throughout the thickness of shank 530. However, in other embodiments, the porosity may increase in a radial direction from an axial center of screw. In even further embodiments, shank 530 may not be entirely porous. Instead, the porous structure may extend inward toward the axis of screw 500 about 0.5 mm or greater from an exterior of shank 530 while the core of shank 530 may be a solid, cylindrical structure which underlies the porous structure of shank 530. In embodiments where a channel extends through screw 500 similar to channel 130 of screw 100, such solid core of shank may form a hollow, cylindrical structure.

The exemplary screws described herein may be formed layer-by-layer using an additive layer manufacturing (ALM), i.e., 3D printing, process so no separate connection mechanism is necessary to bring together any of the components of such bone screws. In some examples, ALM processes are powder-bed based and involve one or more of selective laser sintering (SLS), selective laser melting (SLM), and electron beam melting (EBM), as disclosed in U.S. Pat. Nos. 7,537,664; 8,728,387; 9,180,010; and 9,456,901, the disclosures of which are hereby incorporated by reference in their entireties herein. Assembly of a bone screw with solid and porous portions using ALM is discussed in greater detail below In some arrangements, the above described bone screws are formed using an ALM fabrication process, such as SLS, SLM or EBM described above, fused deposition modeling (FDM), or other appropriate 3D printing technologies known to those skilled in the art. When employing powder-bed based technologies, articles are produced in layer-wise fashion according to a predetermined digital model of such articles by heating, e.g., using a laser or an electron beam, multiple layers of powder, which preferably may be a metallic powder, that are dispensed one layer at a time. The powder is sintered in the case of SLS technology and melted in the case of SLM technology, by the application of laser energy that is directed in raster-scan fashion to portions of the powder layer corresponding to a cross section of the article. After the sintering or melting of the powder on one particular layer, an additional layer of powder is dispensed, and the process repeated, with sintering or melting taking place between the current layer and the previously laid layers until the article is complete. The powder layers similarly may be heated with EBM technology. Additive manufacturing techniques such as the ALM processes described above may be employed to form the solid and porous layers and any other components, as applicable. In some instances, materials for one layer may be different than the materials for successive layers. This process allows for porous portions to extend full thickness through a particular structure, such as the thread 122 of screw 100 and the shank 530 of screw 500, for example. It also allows porous portions to be formed in locations impossible to reach by other methods, such as the liners 227 of screw 200 which are located about channel within screw 200.

Each of solid and porous layers of the above described screws may be constructed from biocompatible metals, such as titanium, titanium alloys, stainless steel, cobalt chrome alloys, tantalum, niobium, another metal, or a biocompatible polymer, such as polyether ether ketone (PEEK). All constituent porous and solid portions of the above described screws may be a common material, such as one of those listed above, or different materials can be employed for each part. Particular combinations of materials and their use for specific parts of herein described bone screws are a matter of design choice and may include the combination of different metals, different polymers, or metals combined with polymers. For example, the solid portions of the herein described screws can be made from a metal while the porous portions may be made from a polymer.

Each of the screws describe herein may have other features that may enhance the function of the screw from those described herein. For example, each of the screws described herein may include serrations on their respective threads. Examples of such serrated threads are described in U.S. application Ser. No. 15/645,264, the disclosure of which is hereby incorporated by reference in its entirety.

Moreover, each of the screws described above are not limited to the particular porous and solid configurations described above. Indeed, each of the above screws can have alternative solid/porous configurations and/or combinations as those previously described. For example, screw 100 may also include the fenestrations 226 described with respect to screw 200. In such an embodiment, thread 122 may have a solid and porous structure as described with relation to screw 100 while also having porous fenestrations distributed in a helical array between thread 122 as described with relation to screw 200. In another example, screw 300 may include the solid/porous thread 122 of screw 100 and/or porous fenestrations 226 of screw 200 in addition to having the porous ring 312 of tulip-shaped head 310.

Also, while the above described solid/porous configurations are associated with particular bone screws, it should be understood that the described solid/porous configurations can be applied to any general purpose bone screw or other specialized bone screws not described herein. Examples of such screws are disclosed in U.S. Pat. No. 6,974,460 and U.S. Publication No. 2017/0086887, the disclosures of which are hereby incorporated by reference herein in their entirety. Moreover, the solid/porous configurations are not limited to screws used in spinal procedures.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A bone fastener comprising:
a head; a shaft extending from the head; and
a thread extending along and about the shaft, the thread having a height extending from a root to a crest thereof, the thread also having first and second portions, the first portion defining the crest, the second portion being disposed between the root and the crest, the second portion being made entirely of a porous structure configured to promote bone ingrowth and having a porosity greater than that of the first portion, the first portion of the thread being positioned further from the shaft than the second portion wherein the head, shaft, and first portion of the thread are made of a solid structure having a porosity smaller than that of the second portion, the solid structure providing strength and stability to the bone fastener.

2. The bone fastener of claim 1, wherein the height of the thread increases toward a distal end of the bone fastener.

3. The bone fastener of claim 2, wherein the shaft tapers inwardly toward the distal end of the bone fastener.

4. The bone fastener of claim 1, wherein the second portion of the thread partially defines an exterior surface of the thread.

5. The bone fastener of claim 1, wherein the first portion and the second portion collectively define an outer bone contacting surface of the thread and the first portion has a solid structure.

6. The bone fastener of claim 1, wherein a height of the second portion is constant along a length of the shaft.

7. The bone fastener of claim 6, wherein a height of the first portion increases toward a distal end of the bone fastener.

8. The bone fastener of claim 7, wherein the height of the thread includes the heights of the first portion and second portion.

9. The bone fastener of claim 1, wherein a height of the second portion is about 0.5 mm or greater.

\* \* \* \* \*